United States Patent
Wang et al.

(10) Patent No.: US 7,259,270 B2
(45) Date of Patent: Aug. 21, 2007

(54) SUPERMOLECULAR CARBOPLATIN DERIVATIVES, THEIR PREPARATION AND PHARMACEUTICAL COMPOSITION CONTAINING THEM AS ACTIVE INGREDIENT AND APPLICATIONS OF THE COMPOSITIONS

(76) Inventors: Jingzun Wang, No. 12-8-601, Yongjinlixiaoqu, 81 Wukesong Road, Haidian District, Bejing, 100039 (CN); Huisheng Qu, No. 12-8-601, Yongjinlixiaoqu, 81 Wukesong Road, Haidian District, Bejing, 100039 (CN); Lei Wang, No. 12-8-601, Yongjinlixiaoqu, 81 Wukesong Road, Haidian District, Bejing, 100039 (CN); Ting Wang, No. 12-8-601, Yongjinlixiaoqu, 81 Wukesong Road, Haidian District, Bejing, 100039 (CN)

( * ) Notice: Subject to any disclaimer, the term of this patent is extended or adjusted under 35 U.S.C. 154(b) by 333 days.

(21) Appl. No.: 10/497,081

(22) PCT Filed: Nov. 30, 2001

(86) PCT No.: PCT/CN01/01595

§ 371 (c)(1),
(2), (4) Date: Mar. 14, 2005

(87) PCT Pub. No.: WO03/045962

PCT Pub. Date: Jun. 5, 2003

(65) Prior Publication Data

US 2005/0165093 A1   Jul. 28, 2005

(51) Int. Cl.
C07F 15/00 (2006.01)
A61K 31/28 (2006.01)
(52) U.S. Cl. .................... 556/137; 514/492
(58) Field of Classification Search ............... 556/137; 514/492
See application file for complete search history.

(56) References Cited

U.S. PATENT DOCUMENTS 6,699,901 B1 * 3/2004 Yang et al. ............... 514/492

OTHER PUBLICATIONS

Wong et al., 1999, "Current Status of Platinum-Based Antitumor Drugs", Chem. Rev., 99: 2451-2466.

Go et al., 1999, "Review of the Comparative Pharmacology and Clinical Activity of Cisplatin and Carboplatin", Journal of Clinical Oncology, vol. 17, No. 1: 409-422.

* cited by examiner

Primary Examiner—Porfirio Nazario-Gonzalez
(74) Attorney, Agent, or Firm—Morgan, Lewis & Bockius LLP

(57) ABSTRACT

The present invention relates to a novel class of supermolecular carboplatin derivatives represented by general formula (I), wherein B is a polycarboxylic acid represented by general formula (II), wherein $R_1$, $R_2$ and n are defined as in the description. The present invention also relates to a process for preparing the same, pharmaceutical compositions containing the same as active ingredient and the use of the derivatives in the preparation of pharmaceutical compositions which are useful in treating various cellular cancers including hepatoma, stomach cancer, lung cancer and the like. The derivatives have stable cage-like chemical structures and constitutions in solid and in aqueous solution. The derivatives can not only kill cancer cells at a rate significantly higher than that by carboplatin, in particular, in the case of hepatoma cells, at a rate one to two times higher than that by carboplatin, but also produce little side effects such as vomit, baldness, decreases of leucocytes and platelets, and the like, which can be induced by administration of other chemotherapeutics. In the acute toxicity tests on mice, the lethal dose ($LD_{50}$) of the present derivatives is about 300 mg/kg and 260 mg/kg body weight for a subcutaneous(sc) and an intraperitoneal(ip) administration, respectively. Therefore, the present derivatives are a novel class of cis-platium which can be widely used as anticancer agents.

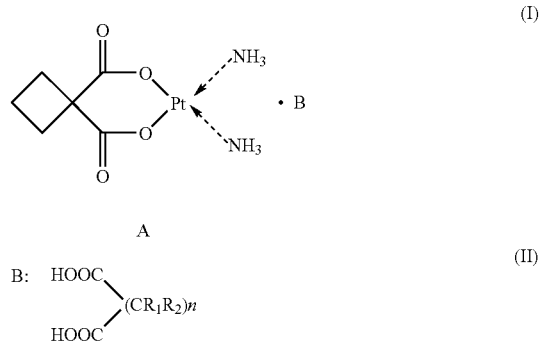

8 Claims, No Drawings

SUPERMOLECULAR CARBOPLATIN DERIVATIVES, THEIR PREPARATION AND PHARMACEUTICAL COMPOSITION CONTAINING THEM AS ACTIVE INGREDIENT AND APPLICATIONS OF THE COMPOSITIONS

CROSS REFERENCE TO RELATED APPLICATIONS

This application is a 371 filing of PCT/CN01/01595 filed Nov. 30, 2001, which is herein incorporated by reference in its entirety.

TECHNICAL FIELD

The present invention relates to a novel class of supermolecular carboplatin derivatives, the preparation of such derivatives, a pharmaceutical composition containing them as active ingredient, and use of the derivatives and pharmaceutical compositions containing them for the clinical treatment of various cellular cancers such as hepatoma, stomach cancer, lung cancer and the like.

BACKGROUND ART

Platinum-containing anticancer drugs have attracted the attention of scientists from many countries since Rosenberg and Camp firstly reported the anticancer effect of cisplatinum[Cis-Pt(NH$_3$)$_2$Cl$_2$] in 1969 (Trans. Met. Chem., 1987: 14, 77). In the last 30 years, tens of platinum-containing anticancerdrugs have been successfully developed and applied in clinical treatment of cancers, such as Iproplatin (GB1578323), Oxaliplatin (J. Med. Chem., 1978:21, 1315), Ormaplatin (J. Med. Chem., 1978:21, 1315), Labaplatin (EP176005), Carboplatin (GB20244823) and the like. However, these drugs are in advantageous in that their stability in aqueous solution is not so good and thus they cannot used in the form of oral preparations; they have high toxicity to human body and thus result in many serious toxic reactions in stomach, kidney, blood and the like. Therefore, novel cisplatinum-derived compounds without the above-mentioned defects have been investigated by pharmaceutical specialists all over the world for many years, but up to now, there is no substantive progress.

In 1978, J. M. Lehn proposed a new concept that weak intermolecular interactions form supermolecular compounds, that is to say, molecules, when bound via a non-covalent force (such as hydrogen bond, coordination bond, van der Waals force, electrostatic attraction, etc.), form molecular aggregates, which exhibit new physicochemical activities such as selectivity, identifiability and migration, and are named as "supermolecular compound". C. J. Peterson, D. J. Cram and Lehn were awarded the Nobel Prize for chemistry in 1987 for their great achievements in supermolecular compounds including crown ethers, cryptands and the like (J. M. Lehn, Angew. Chem., Inter. Ed. Engl., 27, 89, 1988). However, researches concerning the chemical structures of the supermolecular drugs proposed by the present inventors have not been disclosed in prior art.

SUMMARY OF THE INVENTION

Based on the theory of supermolecular chemistry, the present inventors have firstly and successfully designed and synthesized a class of cage-like supermolecular carboplatin anticancer drugs formed by hydrogen and coordination bonds.

Therefore, an object of the present invention is to provide a novel class of supermolecular carboplatin derivatives.

Another object of the present invention is to provide a process for preparing said supermolecular carboplatin derivatives.

Another object of the present invention is to provide a pharmaceutical composition comprising as active ingredient said supermolecular carboplatin derivatives.

Still another object of the present invention is to provide the use of said supermolecular carboplatin derivatives for the clinical treatment of cellular cancers such as hepatoma, stomach cancer, lung cancer and the like.

DETAILED DESCRIPTION OF THE INVENTION

In one aspect, the present invention provides a supermolecular carboplatin derivative represented by general formula (I):

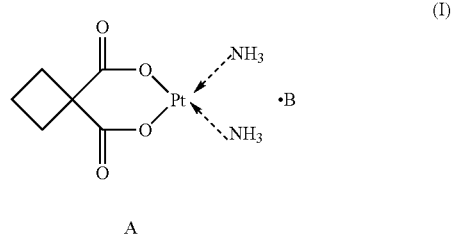

which is a supermolecular compound consisting of a host component A—carboplatin and a guest component B bound via intermolecular hydrogen bonds, wherein the guest component B is a polycarboxylic acid represented by general formula (II):

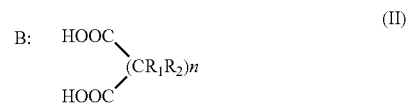

wherein $R_1$ and $R_2$ may be same or different from one another, and independently represent hydrogen, hydroxy, carboxy, phenyl or 3,5-dicarboxyphenyl, n represents an integer of from 0 to 3, with the proviso that $R_1$ and $R_2$ on the same carbon atom cannot be hydroxy or carboxy at the same time, and if n is 2, a double bond may exist between the two carbon atoms, or $R_1$ and $R_2$ may form together with the carbon atom to which they are attached a cyclohexane ring or a benzene ring optionally substituted by one or two further carboxy.

The guest component B is preferably selected from the group consisting of oxalic acid, 1,3-propanedioic acid, 1,4-butanedioic acid, 1,5-pentanedioic acid, cis-butenedioic acid, 2-hydroxy-1,4-butanedioic acid(malic acid), 2,3-dihydroxy-1,4-butanedioic acid(tartaric acid), 2-phenyl-1,3-propanedioic acid, 1,2-dicarboxycyclohexane, 3-hydroxy-3-carboxy-1,5-pentanedioic acid(citric acid), phthalic acid, 1,3,4-benzene-tricarboxylic acid and 1,2,4,5-benzenetetracarboxylic acid, with oxalic acid, 1,3-propanedioic acid, 1,4-butanedioic acid, 2-phenyl-1,3-propanedioic acid, tartaric acid, malic acid or citric acid being more preferred.

Preferably in the compound of general formula (I), the host component A—carboplatin is bound with the guest component B by multiple hydrogen bonds, thereby forming a supermolecular compound with a cage-like spatial structure. For example, when the guest component B is phenylmalonic acid, a supermolecular compound having following general formula (III) is obtained,

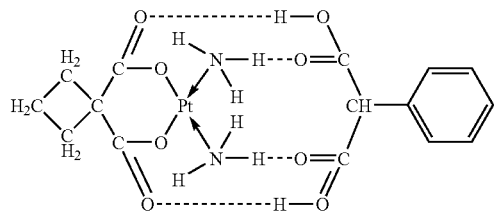

(III)

The supermolecular compound A—B represented by general formula (I) according to the present invention is stable both in solid and in aqueous solution, without dissociation. It is confirmed by spectral analysis, such as UV, IR, NMR, MS, X-ray monomorphic diffraction and the like, that the supermolecular compound according to the present invention is not a mixture, but a novel molecular compound having a single molecular weight, a stable element composition and stable spectral characteristics. The N atom in the intramolecular-$NH_3$ group is in a valence of +5, and thus cannot form a salt (—$NH_4$) with $H^+$; the H atom in the carboxy group of the guest component B forms intramolecular hydrogen bonds with the carbonyl group of the host component A; and at the same time, the H atom in the amino group —$NH_3$ of the host component A forms intramolecular hydrogen bonds with the carbonyl group of the guest component B, thereby constructing the supermolecular compound represented by general formula (I).

In another aspect, the present invention provides a process for preparing the compound represented by general formula (I), which comprises the steps of:
a) preparing aqueous solutions of the host component A—carboplatin and the guest component B, respectively, with their molar concentrations being equal;
b) mixing in equal molar amounts the two starting solutions at a temperature of 4 to 40° C., stirring homogeneously, sterilized and filtered, and
c) diluting the solution obtained in step b) with pure water, followed by direct sealing as an aqueous injection of 50 mg/5 ml, or concentrating the aqueous product solution at a temperature below 40° C. and then drying to form a solid powder.

In the process according to the present invention, the reaction in step b) is preferably carried out at a pH of from 2 to 4, and in order to keep the pH in such a range, a certain amount of component B can be used.

The present invention also relates to a pharmaceutical composition for the treatment of various cellular cancers, comprising as active ingredient the compound represented by general formula (I) according to the present invention and a pharmaceutically acceptable carrier. Said pharmaceutical composition can be formulated into dosage forms such as tablets, capsules, pills, oral solutions and the like.

The present invention further relates to use of the supermolecular compound represented by general formula (I) for the clinical treatment of various cellular cancers such as hepatoma, stomach cancer, lung cancer and the like.

The supermolecular compound represented by general formula (I) according to the present invention exhibits high selectivity for cancer cells. Tests on human cancer cells incubated in vitro show that the supermolecular compound according to the present invention kills various cancer cells such as of liver, stomach, colon, large intestine, pancreas, breast and lung cancer at a rate significantly higher than that by carboplatin, in particular, in the case of hepatoma, at a rate one to two times higher than that by carboplatin, with $IC_{50}$ being about 10-15? g/ml. The test method and the results are shown below.

Method:

The test is carried out in accordance with the internationally accepted pharmacodynamic cytotoxic assay. The drug to be tested is diluted to a desired concentration using 15% fetal calf serum RPMI-1640 medium, filtered and sterilized through an aseptic membrane, and then formulated to provide concentration gradients of 200, 100, 50 and 10? g/ml. The resulting solutions are added to a microtiter plate containing various incubated human cancer cells, and then are incubated for 72 hours. To each well of the plate is added 0.5? 1 0.2% MTT solution, and after 4 hours, DMSO is added to develop color. The absorbance of each well is taken using Model 250 microplate reader, from which the fatality rates of cancer cells and $IC_{50}$ values are calculated.

Results of Fatality Rates of Cancer Cells:

| Concentration ?g/ml | SMAN[1] | SMAM[2] | SMAT[3] | Carboplatin (KP) |
|---|---|---|---|---|
| Fatality rates(%) from MTT test on SMMC-7721 hepatoma cells | | | | |
| 10 | 16.6 | 4.8 | — | — |
| 50 | 23.6 | 22.0 | 8.5 | 2.3 |
| 100 | 44.0 | 25.8 | 15.2 | 11.3 |
| 200 | 75.2 | 67.9 | 51.0 | 28.4 |
| Fatality rates(%) from MTT test on SGC-7921 stomach cancer cells | | | | |
| 10 | 5.8 | — | — | — |
| 50 | 57.5 | 39.4 | 29.2 | 15.0 |
| 100 | 82.0 | 72.0 | 55.8 | 40.0 |
| 200 | 91.0 | 88.6 | 84.4 | 81.0 |
| Fatality rates(%) from MTT test on LS-1747 colon cancer cells | | | | |
| 10 | 3.6 | 2.1 | 7.4 | 2.3 |
| 50 | 12.0 | 2.7 | 10.5 | 7.9 |
| 100 | 54.0 | 41.5 | 36.8 | 11.3 |
| 200 | 69.8 | 56.0 | — | 32.0 |
| Fatality rates(%) from MTT test on PC-14 lung cancer cells | | | | |
| 10 | — | — | — | — |
| 50 | — | — | — | — |
| 100 | 40.9 | 35.7 | 38.0 | 16.3 |
| 200 | 43.7 | 42.6 | 46.0 | 39.4 |
| Fatality rates(%) from MTT test onRCAP-37 human breast cancer cells | | | | |
| 50 | 3.0 | — | — | 2 |
| 100 | 17 | 8 | 6 | 4 |
| 200 | 38 | 23 | 16 | 14.7 |

Note:
[1] supermolecular compound formed by carboplatin and citric acid
[2] supermolecular compound formed by carboplatin and malic acid
[3] supermolecular compound formed by carboplatin and tartaric acid The supermolecular compound represented by general formula (I) according to the present invention exhibits little or no toxic side effects such as vomit, baldness, decreases of leucocytes and platelets, and the like, which can be induced by administration of other chemotherapeutics, and their toxicity on normal human proteins, biomembranes, DNA and RNA is about ½ of carboplatin. For example, the $LD_{50}$ values of the supermolecular compound represented by general formula (I) according to the present invention by subcutaneous injection(sc) and intraperitoneal injection(ip) in albino mice are measured as follows.

Method:

50 Kunming mice weighing 18-22 g are randomized to 5 groups of 10 mice. Single subcutaneous injection(sc) is effected in mice using the drug to be tested at doses of 400, 300, 200, 100, 50 mg/kg. Observation lasts for 14 days, and mortality of each group is recorded. The $LD_{50}$ value is calculated according to Kurber method. Likewise, the $LD_{50}$ value for intraperitoneal injection (ip) is calculated.

Results:

SMAN (supermolecular compound formed by carboplatin and citric acid) is taken by way of example, the $LD_{50}$ values for subcutaneous injection(sc) and intraperitoneal injection (ip) in albino mice are 300 mg/kg and 260 mg/kg, respectively. The mice die after 3 to 7 days.

| | Time of death(days) | | | | | | | |
|---|---|---|---|---|---|---|---|---|
| | 1 | 2 | 3 | 4 | 5 | 6 | 7 | Mortality, % |
| Time of death and mortality(%) in mice(SMAN, s.c.) | | | | | | | | |
| 400 mg/kg | | | 1 | 1 | 2 | 3 | 3 | 100 |
| 300 mg/kg | | | | 1 | 2 | 3 | 1 | 70 |
| 300 mg/kg | | | | | 1 | 3 | 1 | 50 |
| 100 mg/kg | | | | | | | | 0 |
| Time of death and mortality(%) in mice(SMAN, i.p.) | | | | | | | | |
| 400 mg/kg | | | | 1 | 4 | 5 | | 100 |
| 300 mg/kg | | | | | 2 | 3 | | 50 |
| 300 mg/kg | | | | | 1 | | | 10 |
| 100 mg/kg | | | | | | | | 0 |

Although the anticancer mechanism of the compound according to the present invention is not fully determined, it is believed that the following explanations can be made according to the modern molecular biology. The key points of pharmaceutical molecular design lie in that a host component A effective against cancers and a guest component B capable of forming a supermolecular cage with the component A must be present so as to form a supermolecular cage-like compound by coordination and hydrogen bonds, which cage should be relatively stable and not dissociated in aqueous solutions and body fluid, and only when encountering structurally abnormal DNA in cancer cells, become opened due to the induction of free base of the abnormal DNA such as adenine, thereby releasing the active host component A to kill cancer cells. According to such an assumption, the host component A in the present invention is designed to be carboplatin which clinically kills cancer cells and is relatively low in toxicity; and the guest component B should contain polycarboxylic acid group in its structure, and can be bound with the host component A by multiple hydrogen bonds to form the cage-like supermolecule A—B, which retains the relatively stable cage-like structure in body fluid and cells without dissociation, showing no "toxicity" of the host component A to proteins, membranes and normal DNA and RNA. When the supermolecule A—B encounters cancer cells, local hydrogen bonds in the duplex DNA structure in cancer cells would be destructed, thereby exposing free bases, which in turn induces opening of hydrogen bonds in the supermolecule A—B, and the release of the host component A, with the Pt atom in the host component binding to the exposed base of purine in structurally abnormal DNA, thus effectively interrupting the DNA replication and transcription in cancer cells. The procedure can be summarized as below:

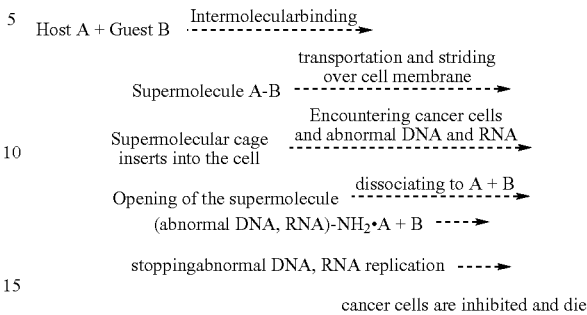

EXAMPLES

The present invention is illustrated in detail by making reference to the following examples, but would not be limited by them.

Example 1

Supermolecular Compound of Phenylmalonic Acid-Carboplatin (SMAP)

Host component A: carboplatin

Guest component B: phenylmalonic acid

Product: supermolecular phenylmalonic acid-carboplatin A—B

Molecular formula: $C_{15}H_{20}O_8N_2Pt$

Molecular weight: 551

Chemical structure:

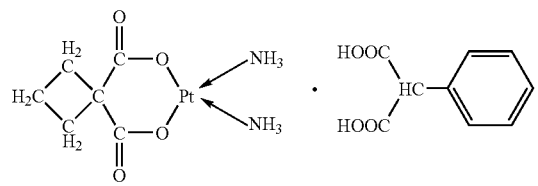

Synthesis:

Preparation of SMAP: 371 parts by weight of starting component A(carboplatin) and 180 parts by weight of starting component B (phenylmalonic acid) are respectively formulated into aqueous solutions of the equal molar concentration. The resulting solutions are then mixed in an equal molar amount at a temperature of 25° C., stirred homogeneously, sterilized and filtered. The aqueous product solution is concentrated at a temperature below 40° C. and dried to afford solid SMAP powder.

Aqueous solution, pH 2.5, T=25° C.

1 mol A+1 mol B --------------------? 1 mol A—B

Appearance:

white crystalline powder; solubility in water: 3.5%; pH: 2.5-3.0; poor solubility in alcohols and other organic solvents; unstable to light and heat.

Spectral Analysis:
  UV: $\lambda_{max}$=245 nm (Aqueous solution);
  IR: KBr disc, main absorption peaks (cm$^{-1}$): 3269 s, 1648 s, 1612 m, 1381 s, 1349 m;
  $^1$H-NMR (500 MHz, DMSO): ?1.6 (2H in host A, quintet), 2.6 (4H in host A, triplet), 4.1 (6H on two N atoms in host A, singlet), 5.8 (CH in guest B), 7.4(5H of benzene ring in guest B), 12.3 (1H of carboxy in guest B);
  MS: ESI-MS, quasi-molecular ion peak M-1 in negative ion mass spectrum: m/z 550.

Pharmacological Activities:
  Fatalityrate of multiple cancer cells in lung cancer, hepatoma and stomach cancer: 50-70%.

Toxicity:
  The LD$_{50}$ by subcutaneous injection(sc) and intraperitoneal injection(ip) in mice are respectively 290 mg/kg and 250 mg/kg.

Stability:
  SMAP can keep stable for a long term in solid and for 8 hours in aqueous solution.

Example 2

Supermolecular Compound of Tartaric Acid-Carboplatin (SMAT)
  Host component A: carboplatin
  Guest component B: tartaric acid
  Product: supermolecular tartaric acid-carboplatin A—B
  Molecular formula: C$_{10}$H$_{18}$O$_{10}$N$_2$Pt
  Molecular weight: 521
  Chemical structure:

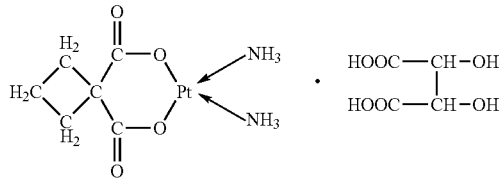

Synthesis:
  Preparation of SMAT: 371 parts by weight of starting component A (carboplatin) and 150 parts by weight of starting component B (tartaric acid) are respectively formulated into aqueous solutions of the equal molar concentration. The resulting solutions are then mixed in an equal molar amount at a temperature of 25° C., stirred homogeneously, sterilized, filtered and diluted with pure water, then directly sealed in the form of an aqueous SMAT injection of 50 mg/5 ml, or the aqueous product solution is concentrated at a temperature below 40° C. and dried to afford solid powder.
  Aqueous solution, pH 2.5, T=25° C.
  1 mol A+1 mol B --------------------? 1 mol A—B Appearance:
  white crystalline powder; solubility in water: 3.5%; pH: 2.5-3.0; poor solubility in alcohols and other organic solvents; unstable to light and heat.

Spectral Analysis:
  UV: ?max=225 nm (shoulder peak, Aqueous solution);
  IR: KBr disc, main absorption peaks (cm$^{-1}$): 3269 s, 1648 s, 1612 m, 1381 s, 1349 m;
  $^1$H-NMR (500 MHz, DMSO): ?1.6 (2H in host A, quintet), 2.6 (4H in host A, triplet), 4.1 (6H on two N atoms in host A, singlet), 4.2 (2CH in guest B), 12.6 (1H of carboxy in guest B);
  MS: ESI-MS, quasi-molecular ion peak M-1 in negative ion mass spectrum: m/z 520.

Pharmacological Activities:
  Fatality rate of multiple cancer cells in lung cancer, hepatoma and stomach cancer: 60-80%.

Toxicity:
  The LD$_{50}$ by subcutaneous injection(sc) and intraperitoneal injection(ip) in mice are respectively 290 mg/kg and 250 mg/kg.

Stability:
  SMAT can keep stable both in aqueous solution and in solid for a long term.

Example 3

Supermolecular Compound of Malic Acid and Carboplatin (SMAM)
  Host component A: carboplatin
  Guest component B: malic acid
  Product: supermolecular malic acid-carboplatin A—B
  Molecular formula: C$_{10}$H$_{18}$O$_9$N$_2$Pt
  Molecular weight: 505
  Chemical structure:

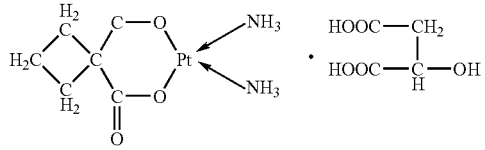

Synthesis:
  Preparation of SMAM: 371 parts by weight of starting component A (carboplatin) and 134 parts by weight of starting component B (malic acid) are respectively formulated into aqueous solutions of the equal molar concentration. The resulting solutions are then mixed in an equal molar amount at a temperature of 25° C., stirred homogeneously, sterilized, filtered and diluted with pure water, then directly sealed in the form of an aqueous SMAM injection of 50 mg/5 ml, or the aqueous product solution is concentrated at a temperature below 40° C. and dried to afford solid powder.
  Aqueous solution, pH 2.5, T=25° C.
  1 mol A+1 mol B ------------------------? 1 mol A—B Appearance:
  white crystalline powder; solubility in water: 3.5%; pH: 2.5-3.0; poor solubility in alcohols and other organic solvents; and unstable to light and heat.

Spectral Analysis:
  UV: ?max=225 nm (shoulder peak, Aqueous solution);
  IR: KBr disc, main absorption peaks (cm$^{-1}$): 3269 s, 1648 s, 1612 m, 1500 m, 1381 s, 1349 m;
  $^1$H-NMR (500 MHz, DMSO): ?1.6 (2H in host A, quintet), 2.6 (4H in host A, triplet), 4.1 (6H on two N atoms in host A, singlet), 4.2 (CH$_2$ in guest B, doublet), 4.3 (CH in guest B, quartet), 12.6 (1H of carboxy in guest B);

MS: ESI-MS, quasi-molecular ion peak M-1 in negative ion mass spectrum: m/z 504.

Pharmacological Activities:
Fatality rate of multiple cancer cells in lung cancer, hepatoma and stomach cancer: 50-80%.

Toxicity:
The $LD_{50}$ by subcutaneous injection(sc) and intraperitoneal injection(ip) in mice are respectively 290 mg/kg and 250 mg/kg.

Stability:
SMAM can keep stable both in aqueous solution and in solid for a long term.

Example 4

Supermolecular Compound of Citric Acid and Carboplatin (SMAN)
Host component A: carboplatin
Guest component B: citric acid
Product: supermolecular citric acid-carboplatin A—B
Molecular formula: $C_{12}H_{20}O_1$, $N_2Pt$
Molecular weight: 563
Chemical structure:

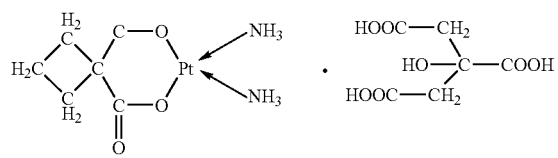

Synthesis:
Preparation of SMAN: 371 parts by weight of starting component A (carboplatin) and 192 parts by weight of starting component B (citric acid) are respectively formulated into aqueous solutions of the equal molar concentration. The resulting solutions are then mixed in an equal molar amount at a temperature of 25° C., stirred homogeneously, sterilized, filtered and diluted with pure water, then directly sealed in the form of an aqueous SMAN injection of 50 mg/5 ml, or the aqueous product solution is concentrated at a temperature below 40° C. and dried to afford solid powder.
Aqueous solution, pH 2.5, T=25?
1 mol A+1 mol B ------------------------? 1 mol A—B Appearance:
white crystalline powder; soluble in water and poorly soluble in alcohols and other organic solvents.

Spectral Analysis:
UV: ?max=225 nm (shoulder peak, Aqueous solution);
IR: KBr disc, main absorption peaks ($cm^{-1}$): 3269 s, 1648 s, 1610 s, 1384 s, 1349 m;
$^1$H-NMR (500 MHz, DMSO): ?1.6 (2H in host A, quintet), 2.6 (4H in host A, triplet), 4.1 (6H on two N atoms in host A, singlet), 4.2 (2 magnetically unequivalent $CH_2$ in guest B), 12.6(1H of carboxy in guest B);
MS: ESI-MS, quasi-molecular ion peak M-1 in negative ion mass spectrum: m/z 562.

Pharmacological Activities:
Fatality rate of multiple cancer cells in lung cancer, hepatoma and stomach cancer: 50-90%.

Toxicity:
The $LD_{50}$ by subcutaneous injection(sc) and intraperitoneal injection(ip) in mice are respectively 300 mg/kg and 260 mg/kg.

Stability:
SMAN can keep stable both in aqueous solution and in solid for a long term.

What is claimed is:
1. A compound represented by general formula (I),

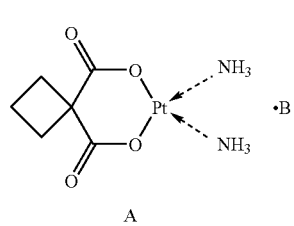

A which is a supermolecular compound consisting of a host component A—carboplatin and a guest component B bound via intermolecular hydrogen bonds, wherein the guest component B is a polycarboxylic acid represented by general formula (II):

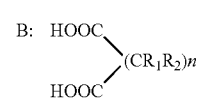

(II)

wherein R1 and R2 may be the same or different from one another, and independently represent hydrogen, hydroxy, carboxy, phenyl or 3,5-dicarboxyphenyl, n represents an integer of from 0 to 3, with the proviso, that $R_1$ and $R_2$ on the same carbon atom cannot be hydroxy or carboxy at the same time, and if n is 2, a double bond may exist between the two carbon atoms, or $R_1$ and $R_2$ may form together with the carbon atom to which they are attached a cyclohexane ring or a benzene ring optionally substituted by one or two further carboxys.

2. The compound represented by general formula (I) according to claim 1, wherein the host component A—carboplatin is bound with a guest component B by multiple hydrogen bonds, thereby constructing a supermolecular compound with a cage-like spatial structure.

3. The compound represented by general formula (I) according to claim 1, wherein the guest component B is selected from the group consisting of oxalic acid, 1,3-propanedioic acid, 1,4-butanedioic acid, 1,5-pentanedioic acid, cis-butenedioic acid, 2-hydroxy-1,4-butanedioic acid (malic acid), 2,3-dihydroxy-1,4-butanedioic acid (tartaric acid), 2-phenyl-1,3-propanedioic acid, 1,2-dicarboxycyclohexane, 3-hydroxy-3-carboxy-1,5-pentanedioic acid (citric acid), phthalic acid, 1,3,4-benzenetricarboxylic acid and 1,2,4,5-benzenetetracarboxylic acid.

4. The compound represented by general formula (I) according to claim 3, wherein the guest component B is oxalic acid, 1,3-propanedioic acid, 1,4-butanedioic acid, phenylmalonic acid, tartaric acid, malic acid or citric acid.

5. The compound of formula (I) according to claim 4, wherein the guest component B is phenylmalonic acid and the supermolecular compound has a structural formula (III):

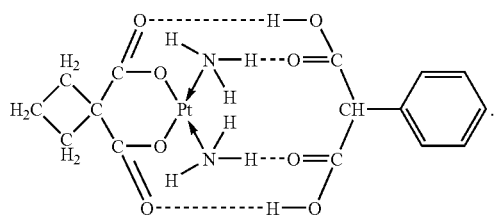
(III)

6. A process for preparing the compound represented for general formula (I) according to claim 1, which comprises the steps of:
   d) preparing aqueous solutions of the host component carboplatin and the guest component B, respectively, with their molar concentrations being equal;
   e) mixing in equal molar amounts the two starting solutions at a temperature of 4 to 40° C., stirring homogeneously, sterilized and filtered, and
   f) diluting the solution obtained in step b) with pure water, followed by direct sealing as an aqueous injection of 50 mg/5 ml, or concentrating the aqueous product solution at a temperature below 40° C. and then drying to form a solid powder.

7. The process according to claim 6, wherein the reaction in step b) is carried out at pH 2-5.

8. A pharmaceutical composition for treating cellular cancers, comprising as active ingredient the compound according to claim 1, and a pharmaceutical acceptable carrier.

* * * * *

UNITED STATES PATENT AND TRADEMARK OFFICE
CERTIFICATE OF CORRECTION

PATENT NO. : 7,259,270 B2  Page 1 of 2
APPLICATION NO. : 10/497081
DATED : August 21, 2007
INVENTOR(S) : Jingzun Wang et al.

It is certified that error appears in the above-identified patent and that said Letters Patent is hereby corrected as shown below:

On the title page, addresses of the inventors, delete "Bejing" and insert -- Beijing --
In column 4, line 10, delete "? g/ml" and insert -- µg/ml --
In column 4, line 18, delete "? g/ml" and insert -- µg/ml --
In column 4, line 22, delete "? l" and insert -- µl --
In column 4, line 32, delete "? g/ml" and insert -- µg/ml --
In column 6, line 62, delete "----------------?" and insert -- ⟶ --
In column 7, line 2, delete "?$_{max}$" and insert -- $\lambda_{max}$ --
In column 7, line 5, delete "?" and insert -- δ --
In column 7, line 58, delete "----------------?" and insert -- ⟶ --
In column 7, line 65, delete "?$_{max}$" and insert -- $\lambda_{max}$ --
In column 8, line 1, delete "?" and insert -- δ --
In column 8, line 35, delete "

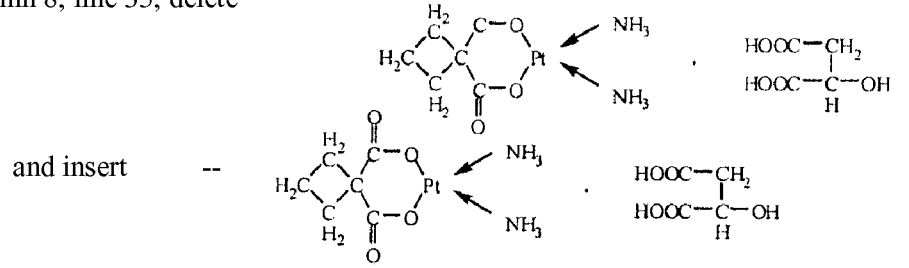

" and insert --

--

In column 8, line 53, delete "----------------?" and insert -- ⟶ --
In column 8, line 64, delete "?" and insert -- δ --
In column 8, line 65, delete "?" and insert -- λ --
In column 9, line 23, delete "$C_{12}H_{20}O_1, N_2Pt$" and insert -- $C_{12}H_{20}O_{11}N_2Pt$ --

In column 9, line 30, delete "

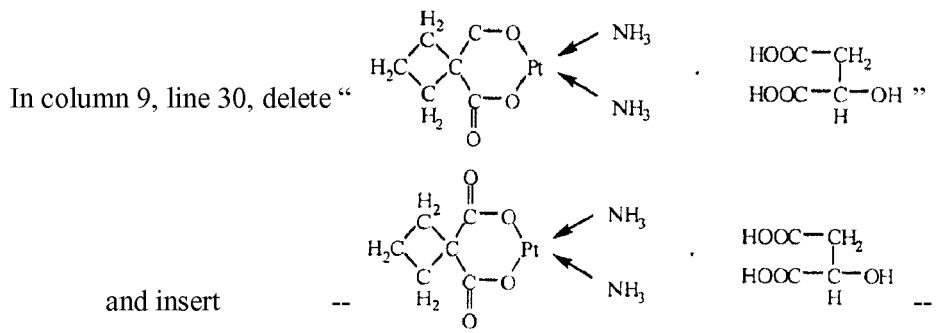

"

and insert --

--

UNITED STATES PATENT AND TRADEMARK OFFICE
CERTIFICATE OF CORRECTION

PATENT NO. : 7,259,270 B2
APPLICATION NO. : 10/497081
DATED : August 21, 2007
INVENTOR(S) : Jingzun Wang et al.

It is certified that error appears in the above-identified patent and that said Letters Patent is hereby corrected as shown below:

In column 9, line 48, delete "?" and insert -- °C --
In column 9, line 49, delete "----------------?" and insert -- 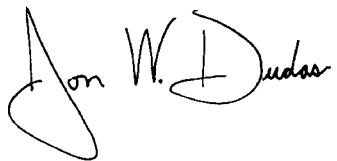 --
In column 9, line 55, delete "?$_{max}$" and insert -- $\lambda_{max}$ --
In column 9, line 58, delete "?" and insert -- δ --
In column 10, line 39, delete "with the proviso, that" and insert -- with the proviso that --
In Claim 6, column 11, line 13, delete "represented for" and insert -- represented by --
In Claim 6, column 11, line 16, delete "d)" and insert -- a) --
In Claim 6, column 12, line 1, delete "e)" and insert -- b) --
In Claim 6, column 12, line 4, delete "f)" and insert -- c) --

Signed and Sealed this

Second Day of September, 2008

JON W. DUDAS
*Director of the United States Patent and Trademark Office*